US009072475B2

(12) United States Patent
Hendriks et al.

(10) Patent No.: US 9,072,475 B2
(45) Date of Patent: Jul. 7, 2015

(54) SPLITTABLE NEEDLE WITH FIBER PROBE

(75) Inventors: Bernardus Hendrikus Wilhelmus Hendriks, Eindhoven (NL); Waltherus Cornelis Jozef Bierhoff, Eindhoven (NL); Gerhardus Wilhelmus Lucassen, Eindhoven (NL); Rami Nachabe, Eindhoven (NL); Theodoor Jacques Marie Ruers, Zeist (NL)

(73) Assignee: Koninklijke Philips N.V., Eindhoven (NL)

( * ) Notice: Subject to any disclaimer, the term of this patent is extended or adjusted under 35 U.S.C. 154(b) by 256 days.

(21) Appl. No.: 13/881,379

(22) PCT Filed: Oct. 17, 2011

(86) PCT No.: PCT/IB2011/054586
§ 371 (c)(1),
(2), (4) Date: Apr. 25, 2013

(87) PCT Pub. No.: WO2012/056363
PCT Pub. Date: May 3, 2012

(65) Prior Publication Data
US 2013/0217989 A1 Aug. 22, 2013

(30) Foreign Application Priority Data
Oct. 27, 2010 (EP) .................................. 10189039

(51) Int. Cl.
*A61B 5/1459* (2006.01)
*A61B 5/00* (2006.01)
*A61M 25/06* (2006.01)

(52) U.S. Cl.
CPC .............. *A61B 5/1459* (2013.01); *A61B 5/0075* (2013.01); *A61B 5/0084* (2013.01); *A61B 5/6848* (2013.01); *A61B 5/6882* (2013.01); *A61M 25/065* (2013.01)

(58) Field of Classification Search
CPC .. A61B 5/1459; A61B 5/0075; A61B 5/0084; A61B 5/6848; A61B 5/6882
See application file for complete search history.

(56) References Cited

U.S. PATENT DOCUMENTS 3,603,311 A * 9/1971 Huggins ....................... 604/161
3,713,442 A 1/1973 Walter
(Continued)

FOREIGN PATENT DOCUMENTS

EP 0628324 12/1994
GB 2278060 11/1994
(Continued)

OTHER PUBLICATIONS

T.J. Farrell et al., "A Diffusion Theory Model of Spatially Resolved, Steady-State Diffuse Reflectance for the Noninvasive Determination of Tissue Optical Properties In Vivo", 1992 Am. Assoc. Phys. Med., Med. Phys. 19(4), Jul./ Aug. 1992, pp. 879-888.
R. Nachabe et al., "Estimation of Lipid and Water Concentrations in Scattering Media With Diffuse Optical Spectroscopy from 900 to 1600 nm", Journal of Biomedical Optics 15(3), May 1/Jun. 2010), pp. 1-1-1-11.

*Primary Examiner* — Eric Winakur (57) ABSTRACT

A needle comprises an elongated first shaft element with a C-shaped cross section and an elongated second shaft element with a C-shaped cross section. The first shaft element and the second shaft element are adapted to be detachably connected to each other. This is achieved by an overlap of respective end sections of the first and second shaft elements. Within the channel formed by the shaft elements, an optical probe may be accommodated from which the shaft elements may be removed by separating the two shaft elements from each other.

6 Claims, 6 Drawing Sheets

(56) References Cited

U.S. PATENT DOCUMENTS

| | | | |
|---|---|---|---|
| 4,702,735 A | 10/1987 | Luther et al. | |
| 4,921,479 A * | 5/1990 | Grayzel | 604/509 |
| 5,135,501 A * | 8/1992 | Cameron | 604/161 |
| 5,281,204 A | 1/1994 | Horie et al. | |
| 5,667,514 A * | 9/1997 | Heller | 606/108 |
| 6,585,703 B1 | 7/2003 | Kassel et al. | |
| 2004/0064147 A1 | 4/2004 | Struble | |
| 2010/0262216 A1 * | 10/2010 | Xue | 623/1.2 |

FOREIGN PATENT DOCUMENTS

| | | |
|---|---|---|
| WO | WO9951143 | 10/1999 |
| WO | WO2009129186 | 10/2009 |

* cited by examiner

SPLITTABLE NEEDLE WITH FIBER PROBE

FIELD OF THE INVENTION

The invention generally relates to a splittable needle. Particularly, the invention relates to a splittable needle with fiber probe for tissue inspection based on for example optical spectroscopy.

BACKGROUND OF THE INVENTION

In the field of oncology, chemotherapy is in most cases applied in order to treat the cancer. Various chemo-medications exist and their effectiveness depends strongly on the type of tumor. The tumors are in general divers and as a result, the effectiveness of the chemo-medication is difficult to predict. Currently, only after weeks, the effectiveness can be determined, for instance with PET-CT. Timely determining of the effectiveness is important in order not to lose time in treating the tumor and to reduce costs of the chemotherapy.

In order to introduce a suprapub catheter in the bladder, splittable needles are used in the field of urology. An example is the Cystofix of the company B. Braun. They have a needle that contains a rolled tear line that enables the splitting of the needle in two parts. There are two drawbacks of this construction. At one side, the rolled tear line is not along the complete needle. This makes splitting the needle difficult at the part where the tear line stops. Furthermore, this means that splitting of the needle can only be performed when it is completely outside the body. After splitting the needle the edges are very sharp and may have a risk of causing harm to the patient or the physician. Certainly, the needle cannot be partly split to create a temporally opening to the side to perform measurements or to perform treatments.

From GB 2 278 060 A, a needle for introducing a catheter is known which is splittable, so that it can be removed after the catheter has been inserted. The needle has two longitudinally extending notches on opposite sides thereof which allow the needle to be split into halves. The already pre-split ends of the needle are inserted into a sleeve which can also be split into two longitudinal halves by means of grooves. The splitting process in initiated by moving two fins projecting radially from each half of the sleeve towards one another. After a partial splitting of the sleeve along the groove one or more projections on the fins meet and continued movement of the fins towards one another causes the sleeve to split along the groove. Partially opening the needle is not possible in this construction.

SUMMARY OF THE INVENTION

It might be an object of the invention to provide a needle which may be easily split along the shaft of the needle, and which is adapted to accommodate a probe. This might be achieved by the subject-matter according to each of the independent claims. Further embodiments of the present invention are described in the respective dependent claims.

In general, a needle according to the invention comprises an elongated first shaft element with a C-shaped cross section including a first middle section between two first end sections in a circumferential direction, and an elongated second shaft element with a C-shaped cross section including a second middle section between two second end sections in a circumferential direction. The first shaft element and the second shaft element are adapted to be detachably connected to each other. This is achieved by an overlap of the respective end sections of the first and second shaft elements.

The end sections of the first shaft element and the second shaft element may be curved to a certain degree to ensure that the overlapping end sections reliably connect the two shaft elements to each other.

To achieve a predetermined position of the first shaft element relative to the second shaft element, the first shaft element may further include an inward-projection between the middle section and each of the end sections, so that, when the first and second shaft element are connected to each other, the overlapping of the two end sections of the first and second shaft elements is limited by the two inward-projections.

On the other hand, the second shaft element may further include an outward-projection between the middle section and each of the end sections, so that, when the first and second shaft elements are connected to each other, the overlapping of the two end sections of the first and second shaft elements is limited by the two outward-projections.

It should be noted, that also a combination of the inward-projections and the outward-projections may be provided to achieve the well-defined positioning of the first shaft element relative to the second shaft element, when these elements are assembled.

Since the first and second shaft elements are both C-shaped elements, and since these elements overlap partially, a hollow channel within the shaft elements is formed, wherein a probe body may be movably accommodated within this channel.

The connection according to the invention between the two shaft elements allows for a movement of the first shaft element in an axial direction of the needle relative to the second shaft element, or vice versa. By way of this, it may be possible to expose at least a portion of the inner space to the side, and thus it may be possible to expose at least a portion of a side surface of the probe body for further functionalities.

In accordance with another embodiment of the invention, the probe body includes optical fibers the first end of which may be located at the tip portion of the probe body for an inspection of tissue surrounding the tip portion of the probe body. The other ends of the optical fibers may be connected by means of a connector to a console containing a light source and a light detector for detecting tissue characteristics at the distal end of the probe.

According to a further embodiment of the invention, the probe body includes channels for fixation wires for anchoring the tip portion of the probe body within a tissue. The wires may be movably arranged within the channels in the probe body and may be made out of a kind of shape memory material like spring steel. Therefore, each wire may be pre-stressed in a curved configuration, so that the wire when protruding out of the distal tip, i.e. out of the open end of one of the channels at the distal tip of the probe body will return to its curved configuration and thus form hook-like elements for a fixation of the tip portion of the probe.

According to another embodiment of the invention, a system is provided including a splittable needle as described above and a tissue inspection device which may comprise a console for spectroscopy, wherein optical fibers located within a probe body may be connected with this console.

According to yet another embodiment of the invention, a method of use of a splittable needle in accordance with the invention generally comprises the steps of positioning the tip portion of the needle including the probe body at a desired position within a tissue, anchoring the probe body within the tissue by means of the wires, pulling back the shaft elements, connected to each other, out of the tissue and removing the shaft elements of the needle by splitting the elements. Such an introduced probe body will not harm or injure the surrounding tissue, as a stiff needle would do, and will thus be comfortable for a long-term treatment.

It has to be noted that embodiments of the invention are described with reference to different subject-matters. In particular, some embodiments are described with reference to method steps, whereas other embodiments are described with reference to devices. However, a person skilled in the art will gather from the above and the following description that, unless other notified, in addition to any combination of features belonging to one type of subject-matter also any combination between features relating to different subject-matters is considered to be disclosed with this invention.

The aspects defined above and further aspects, features and advantages of the present invention can also be derived from the examples of embodiments to be described hereinafter and are explained with reference to examples of the embodiments. The invention will be described in more detail, but will not be limited to the examples of the following embodiments.

BRIEF DESCRIPTION OF THE DRAWINGS

The illustrations and the drawings are schematically only and not to scale. It is noted that in different figures, similar elements are provided with the same reference signs.

DETAILED DESCRIPTION OF EMBODIMENTS

Figure 1:
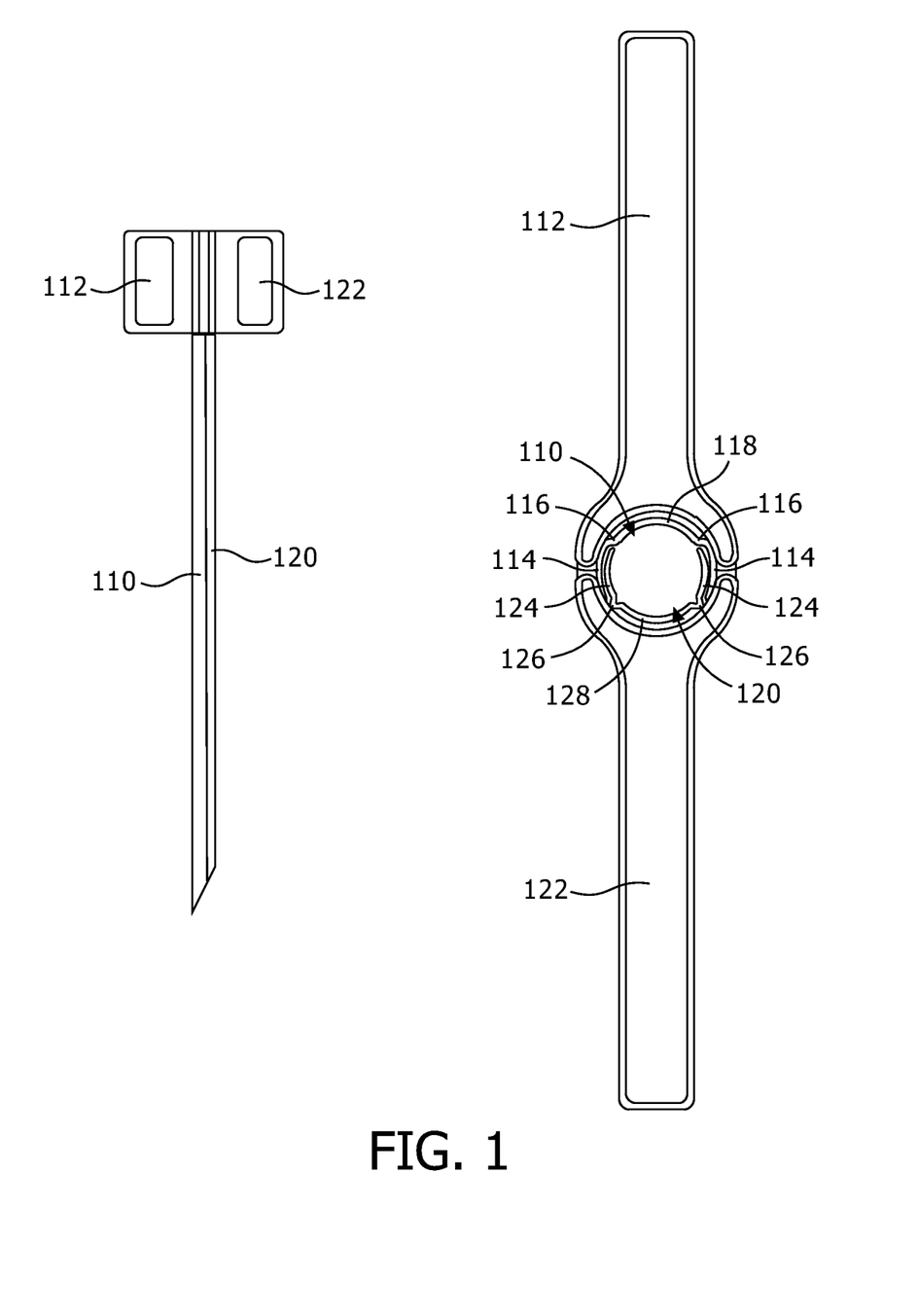
FIG. 1 illustrates a side view of a splittable needle as well as an enlarged top view of the gripping portions of the needle, according to the invention.

In FIG. 1, illustrations of the splittable needle according to the invention are shown. The needle consists of two parts, i.e. a first shaft element 110 and a second shaft element 120. The second shaft element is partly enclosed by the first shaft element. At the proximal end of the splittable needle, gripping portions are provided. A first holder part 112 is attached to the first shaft element 110, whereas a second holder part 122 is attached to the second shaft portion 120. By way of pulling the gripped holder parts away from each other, the shaft elements may be easily separated from each other.

A reliable connection between the first and second shaft elements is realized by an overlap of the end portions 114 of the first shaft element 110 over the end portions 124 of the second shaft element 120. Additionally, inward-projections 116 are provided between each of the first end sections 114 and a middle section 118 of the first shaft element. Furthermore, the second shaft element 120 includes bulks or projections 126 between the two end sections 124 and a middle section 128, in order to make it robust and to provide stabilization so that the two shaft elements cannot rotate with respect to each other.

Furthermore, due to the construction of the invention, the two shaft elements 110, 120 can be torn apart or can slide with respect to each other in the longitudinal direction. This enables that the needle can be split in two, the needle parts can be partially shifted with respect to each other to create an opening to the side or the two separate shaft elements can be reassembled if necessary. The holder parts 112, 122 of the needle may contain additional functionalities apart from the functionality to be able to easily separate the two parts of the splittable needle.

Figure 2:
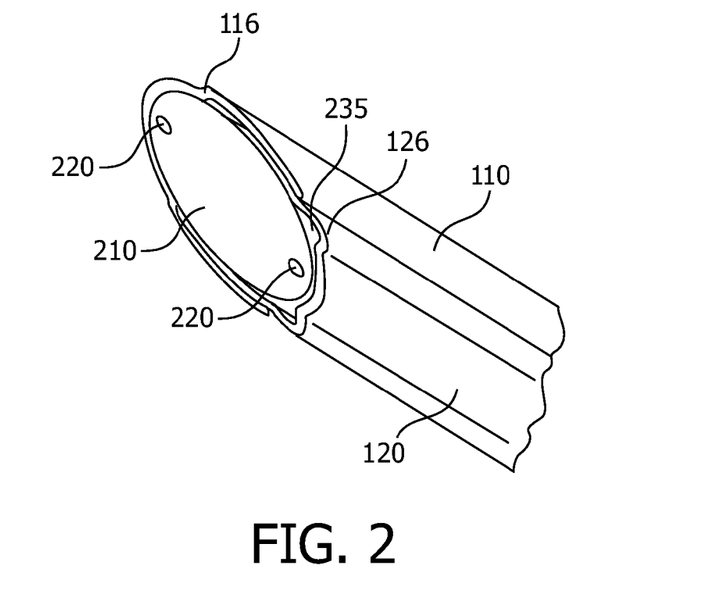
FIG. 2 shows a tip portion of a splittable needle with a probe body according to the invention.

As can be seen in FIG. 2, the distal tip portion of the two shaft elements 110, 120 as well as a probe body 210 are slanted to form a needle tip capable of being easily introduced into tissue. In the probe body 210, a first optical fiber 220 is located adjacent to the distal end of the slanted front surface of the probe body, and a second optical fiber 220 is located at the proximal end of the slanted surface of the probe body. Therefore, the two fibers may be arranged as far as possible away from each other on the slanted surface. One fiber may deliver light to the distal end of the probe body while the other fiber may collect the scattered light and may guide this light towards a detector in a console for spectroscopy.

It is noted, that the optical fibers 220 may be directly embedded in the probe body 210 or placed in channels formed in the probe body, at the above described positions. Alternatively each of the optical fibers 220 may be located within a duct 235 which is formed between an outward projection 126 of the second shaft element 120 and an outer surface of the probe body 210, instead of within the probe body.

It is noted that additional fibers or other functionality like ablation or suction may be easily integrated within the duct 235. Furthermore, the duct 235 may be utilized to extract a fluid, cells or tissue or to inject substances like pharmaceuticals.

Figure 3:
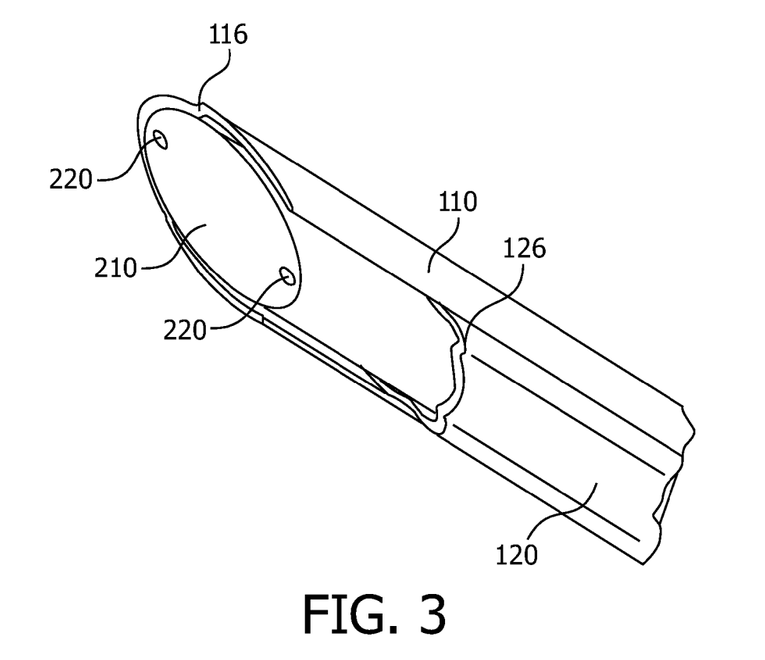
FIG. 3 shows a tip portion of a splittable needle according to the invention, with one shaft element pulled back relative to the other shaft element.

In FIG. 3, an exemplary illustration of the splittable needle is shown, with the second shaft element 120 slide ably pulled back relative to the first shaft element 110, so that a portion of the side surface of the probe body 210 inside the splittable needle is exposed to the tissue surrounding the needle. This allows side way inspection of the tissue. This is of particular interest when tissue is sensitive to bleedings, for instance in the lung. In this case voids in front of the needle can easily fill up with blood making optical inspection of the tissue influenced by this bleeding. When looking to the side this effect is less apparent because the tissue is usually pressed firmly to the side of the needle avoiding voids filled with blood.

Figure 4:
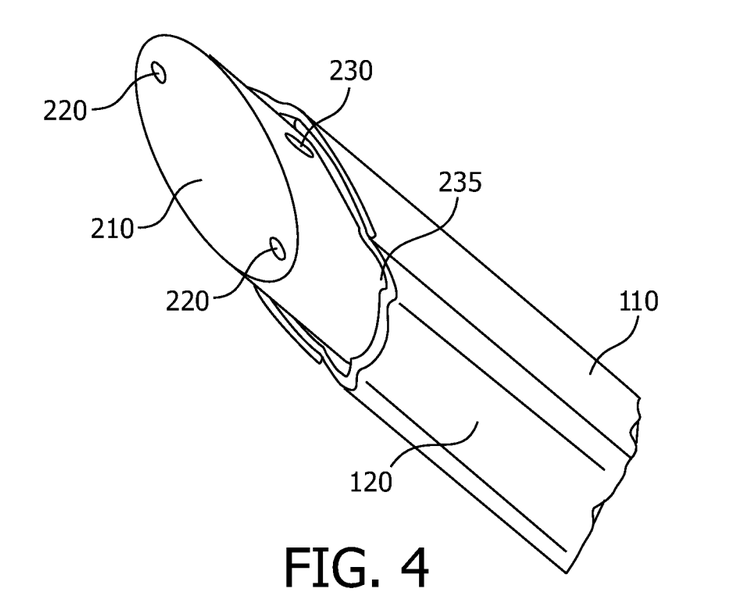
FIG. 4 shows a tip portion of a splittable needle according to the invention, with both shaft elements pulled back so that the end portion of the probe body protrudes from the shaft elements.

In FIG. 4, both shaft elements 110, 120 of the splittable needle are pulled back so that openings of channels 230 in the circumferential surface of the probe body 210 are exposed. Such channels 230 with openings in the circumferential surface of the probe body 210 may be used for anchoring wires 240. An end of a wire 240 may be moved out of such an opening to form a fixation means for fixation of the probe body 210 within a tissue.

Figure 5:
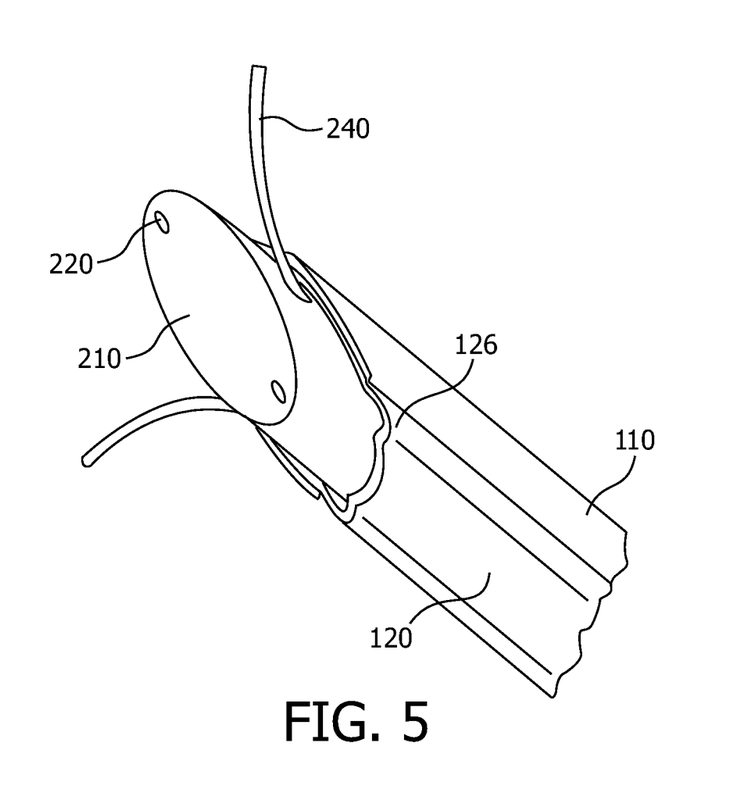
FIG. 5 shows the tip portion of a splittable needle as in FIG. 4, with fixation wires protruding from the end portion of the probe body.

FIG. 5 illustrates a tip portion of a splittable needle with fixation wires 240 protruding out of the probe body 210. Each fixation wire consists of a curved metal part that when moved with respect to the probe body will extrude to the side of the probe body away from the optical fiber ends. Due to the curvature of the metal part the wire will curl into the tissue giving rise to a firm fixation of the probe. It is noted that the fixation wires may also be in the shape of a corkscrew. In this case the fixation wire is turned such that the corkscrew part screws inside the tissue again providing a firm fixation.

Figure 6:
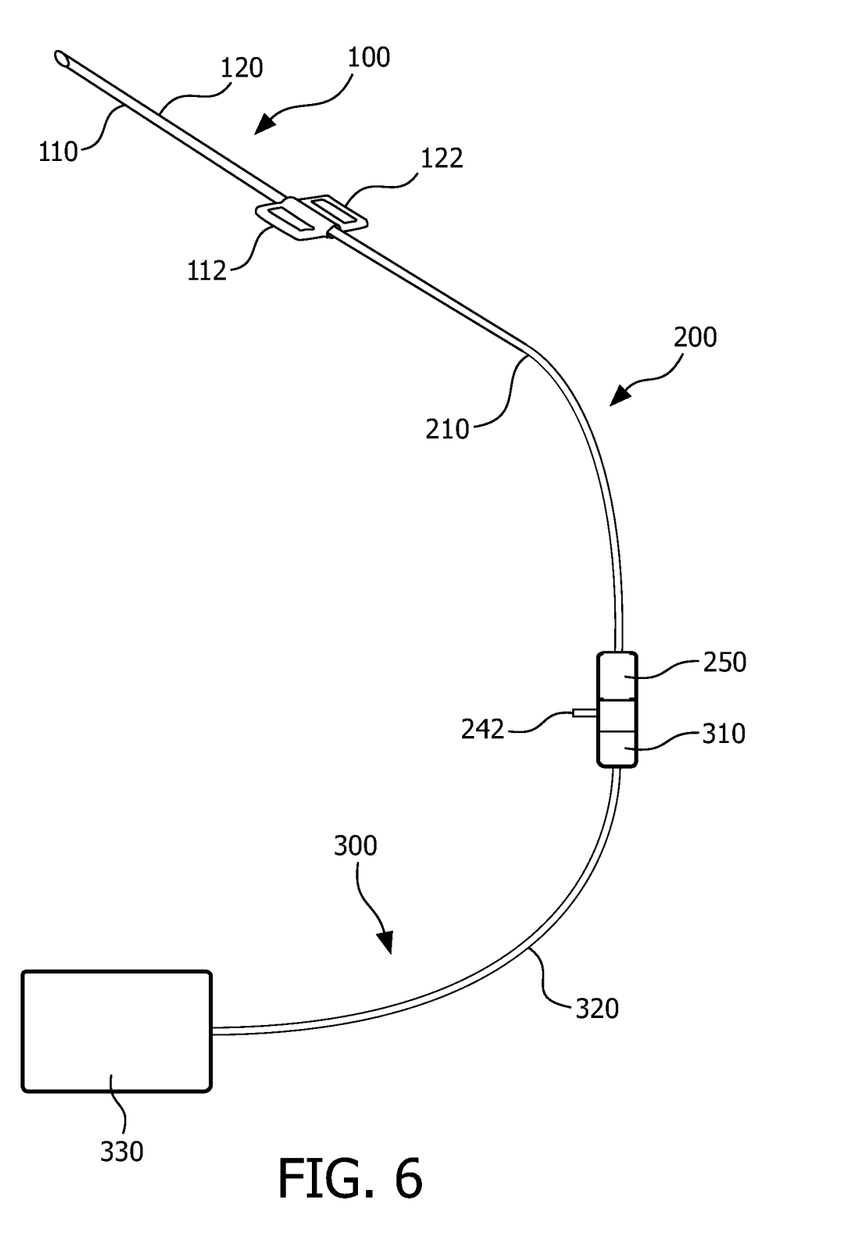
FIG. 6 is an illustration of a splittable needle together with a probe connected to a console for tissue inspection.

In FIG. 6, a system according to the invention is shown including a splittable needle 100 and a device for tissue inspection 300. Within the two shaft elements 110, 120, an optical probe 200 is located, wherein the probe body 210 may be elastical or flexible. At the proximal end of a probe body 210, a connector 250 is provided for a connection of especially the ends of the optical fibers provided within the probe body. Additionally, for example at a side of the connector 250, an actuation element 242 may be arranged for an actuation, i.e. a shifting of the fixation wire within the probe body in a longitudinal direction, so that the distal end of the fixation wire may protrude out of the distal end of the probe body, as shown in FIG. 5.

The optical probe 200 is connected to a tissue inspection device 300 by way of a connector 250 at the probe body 210 which is connected with a connector 310 at an end of an optical cable 320 leading to a console 330 including a light source and a light detector. The light source of the console 330 enables light to be provided via one of the fibers to the distal end of the optical probe 200. The light scattered by tissue is collected by the other fiber and is guided towards the light detector.

The data are processed using a dedicated algorithm. For instance light is coupled out of the distal tip through at least one fiber, which serves as a source, and the wavelength is swept from e.g. 500-1600 nm. The corresponding wavelength-dependent reflection is measured by at least one other fiber, which is spatially separated from the source at e.g. 1-2 mm. The amount of reflected light measured at the "detection" fiber, is determined by the absorption and scattering properties of the probed structure (e.g. tissue). Upon spatial and temporal (wavelength-dependent) multiplexing, reflections can be measured at multiple sites of the electrode tip.

Although diffuse reflectance spectroscopy is described above to extract tissue properties also other optical methods can be envisioned like fluorescence spectroscopy measurement, diffuse optical tomography by employing a plurality of optical fibers, differential path length spectroscopy, or Raman spectroscopy.

Figure 7:
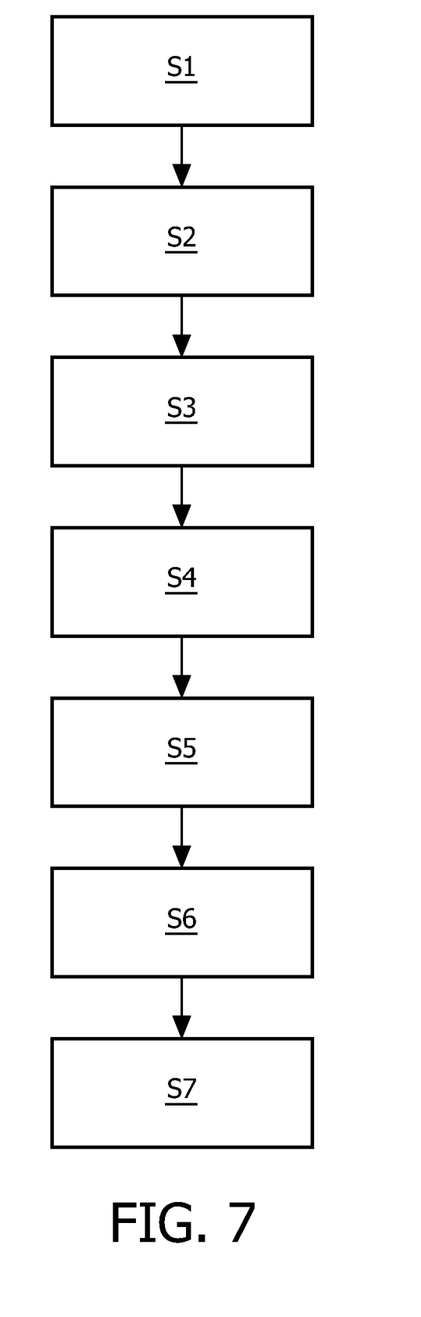
FIG. 7 is a flowchart of a method for use of the splittable needle in accordance with the invention.

FIG. 7 is a flow chart, showing the steps of a method of the use of the splittable needle together with an optical probe according to the invention. It will be understood, that the steps described with respect to the method are major steps, wherein these major steps might be differentiated or divided into several sub-steps. Furthermore, there might be also sub-steps between these major steps. Therefore, a sub-step is only mentioned, if that step is important for the understanding of the principles of the method according to the invention.

In step S1, the splittable needle with the optical probe inside is introduced percutaneously through the tissue to a desired position within the tissue.

In step S2, the signal from the optical probe is used to confirm that the probe tip is inside tumor tissue, for example.

In step S3, at least one fixation wire is employed to firmly fixate the probe tip in the tissue.

In step S4, the splittable needle is retraced back out of the tissue.

In step S5, the splittable needle is split in two shaft elements and is removed, wherein the probe remains in the body.

In step S6, the probe is used to measure the tissue properties over time when administering for example chemotherapy.

In step S7, when the treatment shows a positive response, the optical probe is removed by first retracing the fixation wires and then the optical probe itself.

In the following, an algorithm is described by means of which optical tissue properties such as the scattering coefficient and absorption coefficient of different tissue chromophores: e.g. hemoglobin, oxygenated haemoglobin, water, fat, etc. may be derived. These properties may be different for healthy tissue compared to diseased tissue such as tumor tissue and can be used to discriminate healthy from diseased tissue. This can be useful for positioning the optical insert at the correct location. For instance correct placement of the optical insert tip in the tumor for tumor response measurement on chemotherapy.

Another application may be when tissue is treated by for instance ablation. In this case the progress of the tissue ablation can be followed by the optical probe.

In more detail the algorithm can be described as follows. The spectral fitting will be performed by making use of the analytically derived formula for reflectance spectroscopy (see Ref [T. Farrell et al. 'A diffusion theory model of spatially resolved steady-state diffuse reflectance for non-invasive determination of tissue optical properties in vivo', Med. Phys. 19 (1992), page 879-888]). A detailed description of the algorithm can be found in the paper by R. Nachabe, et al., "Estimation of lipid and water concentrations in scattering media with diffuse optical spectroscopy from 900 to 1600 nm" in Journal of Biomedical Optics volume 15 (3), 2010, page 037015 that we include by reference. This reflectance distribution R is given by $$R(\rho) = \int_0^\infty R(\rho, z_0) \delta(z_0 - 1/\mu_t') dz_0 \qquad (1)$$
$$= \frac{a'}{4\pi} \left[ \frac{1}{\mu_t'} \left( \mu_{eff} + \frac{1}{\tilde{r}_1} \right) \frac{e^{-\mu_{eff}\tilde{r}_1}}{\tilde{r}_1^2} + \left( \frac{1}{\mu_t'} + 2z_b \right) \left( \mu_{eff} + \frac{1}{\tilde{r}_2} \right) \frac{e^{-\mu_{eff}\tilde{r}_2}}{\tilde{r}_2^2} \right]$$

with $$\tilde{r}_1 = [x^2 + y^2 + (1/\mu_t')^2]^{1/2}$$
$$\tilde{r}_2 = [x^2 + y^2 + ((1/\mu_t') + 2z_b)^2]^{1/2}$$
$$\mu_{eff} = \sqrt{3\mu_a[\mu_a + \mu_s(1-g)]}$$

In this formula the three macroscopic parameters describing the probability of interaction with tissue are: the absorption coefficient $\mu_a$ and the scattering coefficient $\mu_s$ both in $cm^{-1}$ as well as by g which is the mean cosine of the scattering angle. Furthermore, we have the total reduced attenuation coefficient $\mu_t'$ that gives the total chance for interaction with tissue $$\mu_t' = \mu_a + \mu_s(1-g). \qquad (2)$$

The albedo a' is the probability of scattering relative to the total probability of interaction $$a' = \mu_s'/\mu_t'. \qquad (3)$$

A point source at a depth $z_0 = 1/\mu_t'$ and no boundary mismatch hence $z_b = 2/(3\mu_t')$ are assumed. Furthermore, it is assumed that the scattering coefficient can be written as $$\mu_s'(\lambda) = a\lambda^{-b} \qquad (4)$$

Figure 8:
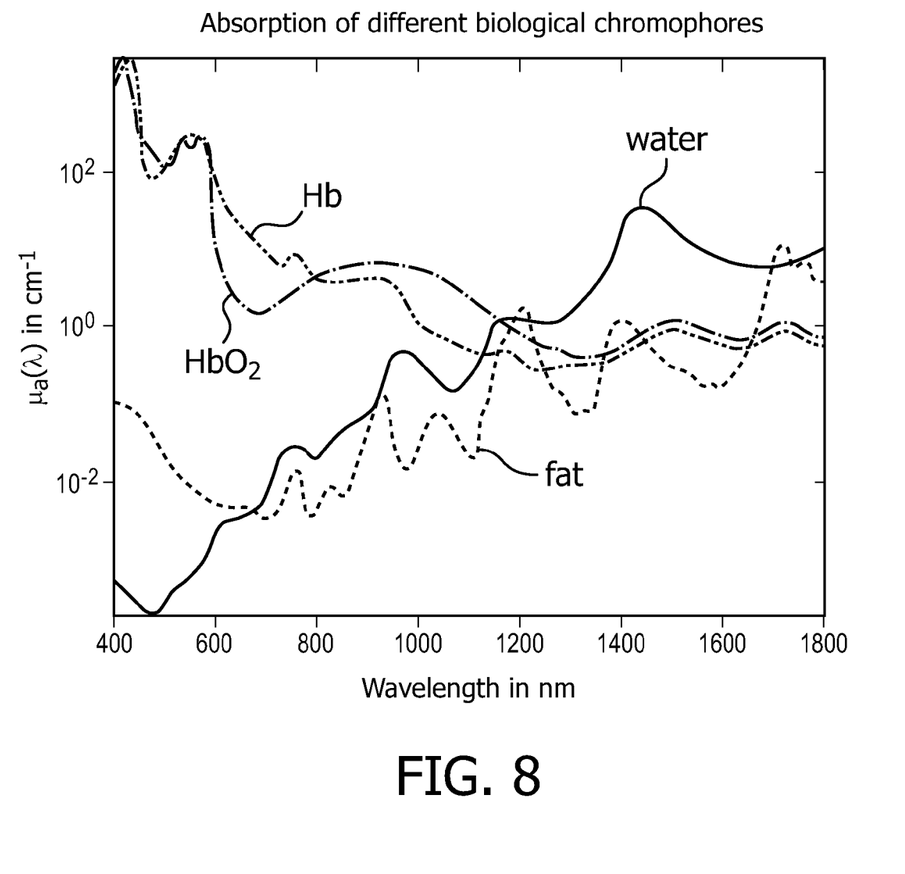
FIG. 8 shows the absorption coefficient of chromophores as a function of wavelength.

The main absorbing constituents in normal tissue dominating the absorption in the visible and near-infrared range are blood (i.e. hemoglobin), water and fat. In FIG. 8, the absorption coefficient of these chromophores as a function of the wavelength is presented. Note that blood dominates the absorption in the visible range, while water and fat dominate in the near infrared range.

The total absorption coefficient is a linear combination of the absorption coefficients of for instance blood, water and fat (hence for each component the value of that shown in FIG. 8 multiply by its volume fraction). By fitting the above formula while using the power law for scattering we can determine the volume fractions of the blood, water and fat as well as the scattering coefficient. With this method we can now translate the measured spectra in physiological parameters that can be used to discriminate different tissues.

Another way to discriminate differences in spectra is by making use of multivariate statistical analysis methods such as principal component analysis which render classification of differences in spectra and thus allows discrimination between tissues.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. Any reference signs in the claims should not be construed as limiting the scope.

LIST OF REFERENCE SIGNS

100 Splittable needle
110 First shaft element
112 First holder part
114 First end section
116 Inward-projection
118 First middle section
120 Second shaft element
122 Second holder part
124 Second end section
126 Outward-projection
128 Second middle section
200 Optical probe
210 Probe body
220 Optical fiber
230 Channel
235 Duct
240 Fixation wire
242 Actuation means
250 Connector
300 Tissue inspection device
310 Connector
320 Cable
330 Console

The invention claimed is:

1. A needle comprising
an elongated first shaft element with a C-shaped cross section including a first middle section between two first end sections in a circumferential direction,
an elongated second shaft element with a C-shaped cross section including a second middle section between two second end sections in a circumferential direction, wherein the first shaft element and the second shaft element are adapted to be detachably connected to each other, so that the first end sections overlap with the respective second end sections,
an elongated probe body which is movably accommodatable in an inner space formed by the first and second shaft elements when connected to each other,
wherein the second shaft element further includes an outward-projection between the second middle section and each of the second end sections, wherein each of the outward-projections forms a duct, and wherein, when the first and second shaft elements are connected to each other, the overlapping of the end sections of the first and second shaft elements is limited by the outward-projections.

2. The needle of claim 1, wherein the first shaft element (110) further includes an inward-projection between the middle section and each of the end sections, and wherein, when the first and second shaft elements are connected to each other, the overlapping of the end sections of the first and second shaft elements is limited by the inward-projections.

3. The needle (100) of claim 1, further comprising optical fibers (220) for transmitting light along the probe body (210) in a longitudinal direction.

4. The needle (100) of claim 1, wherein the optical probe includes a fixation wire for anchoring the probe body of the optical probe within a tissue.

5. A system including
a needle according to claim 1, and
a tissue inspection device.

6. The system of claim 5, wherein the tissue inspection device comprises a console for spectroscopy.

* * * * *